(12) United States Patent
Birkenbach et al.

(10) Patent No.: US 9,622,832 B2
(45) Date of Patent: Apr. 18, 2017

(54) SURGICAL INSTRUMENT, IN PARTICULAR POINTER INSTRUMENT, COMPRISING TIP SENSOR

(75) Inventors: Rainer Birkenbach, Erding, DE (US); Stefan Vilsmeier, Münich (DE)

(73) Assignee: Brainlab AG, Munich (DE)

( * ) Notice: Subject to any disclaimer, the term of this patent is extended or adjusted under 35 U.S.C. 154(b) by 824 days.

(21) Appl. No.: 12/562,163

(22) Filed: Sep. 18, 2009

(65) Prior Publication Data

US 2010/0076455 A1 Mar. 25, 2010

Related U.S. Application Data

(60) Provisional application No. 61/104,799, filed on Oct. 13, 2008.

(30) Foreign Application Priority Data

Sep. 19, 2008 (EP) ..................... 08164701

(51) Int. Cl.
| | |
|---|---|
| A61B 19/00 | (2006.01) |
| A61B 90/96 | (2016.01) |
| A61B 90/98 | (2016.01) |
| A61B 17/00 | (2006.01) |
| A61B 90/00 | (2016.01) |
| A61B 34/20 | (2016.01) |

(52) U.S. Cl.
CPC .............. *A61B 90/96* (2016.02); *A61B 34/20* (2016.02); *A61B 90/98* (2016.02); *A61B 2017/00411* (2013.01); *A61B 2017/00464* (2013.01); *A61B 2017/00482* (2013.01); *A61B 2017/00734* (2013.01); *A61B 2034/2051* (2016.02); *A61B 2034/2068* (2016.02); *A61B 2090/064* (2016.02); *A61B 2090/065* (2016.02); *A61B 2090/0806* (2016.02)

(58) Field of Classification Search
CPC ...................... A61B 17/00234; A61B 1/00101
USPC .................................. 606/1, 10, 13; 607/88
See application file for complete search history.

(56) References Cited

U.S. PATENT DOCUMENTS

| | | | | |
|---|---|---|---|---|
| 4,199,245 | A | * | 4/1980 | Nakai ..................... G03B 7/26 396/263 |
| 5,769,791 | A | * | 6/1998 | Benaron et al. .............. 600/473 |
| 6,021,343 | A | * | 2/2000 | Foley et al. .................. 600/429 |

(Continued)

FOREIGN PATENT DOCUMENTS

| | | |
|---|---|---|
| CA | 2 364 122 | 9/2000 |
| DE | 299 04 018 U1 | 6/1999 |

(Continued)

OTHER PUBLICATIONS

European Office Action for Application No. 08164701.8 dated Aug. 11, 2010.

*Primary Examiner* — William Thomson
*Assistant Examiner* — John R Downey
(74) *Attorney, Agent, or Firm* — Tucker Ellis LLP

(57) ABSTRACT

The invention relates to a surgical instrument comprising a handle portion and a tip, wherein a tip sensor is provided on the handle portion. The tip sensor enables detection of when a tip is inserted into and/or removed from the handle. In addition, the tip sensor enables a navigation system to be notified when landmarks are probed with the surgical instrument, thereby ensuring accurate capture of the location of the landmark.

21 Claims, 2 Drawing Sheets

(56) References Cited

U.S. PATENT DOCUMENTS

| | | | |
|---|---|---|---|
| 6,236,880 B1 * | 5/2001 | Raylman et al. | 600/436 |
| 6,434,507 B1 * | 8/2002 | Clayton et al. | 702/152 |
| 7,744,605 B2 | 6/2010 | Vilsmeier et al. | |
| 7,840,256 B2 * | 11/2010 | Lakin et al. | 600/426 |
| RE43,328 E * | 4/2012 | Foley et al. | 600/429 |
| 2003/0055360 A1 * | 3/2003 | Zeleznik et al. | 600/587 |
| 2003/0069588 A1 * | 4/2003 | Vilsmeier et al. | 606/116 |
| 2005/0124988 A1 * | 6/2005 | Terrill-Grisoni et al. | 606/53 |
| 2006/0095096 A1 * | 5/2006 | DeBenedictis et al. | 607/88 |
| 2006/0142656 A1 | 6/2006 | Malackowski et al. | |
| 2007/0050030 A1 * | 3/2007 | Kim | A61B 17/7059 623/17.11 |
| 2007/0213692 A1 | 9/2007 | Neubauer et al. | |
| 2008/0009697 A1 | 1/2008 | Haider et al. | |
| 2008/0200927 A1 | 8/2008 | Hartmann et al. | |
| 2009/0131922 A1 * | 5/2009 | Dewey et al. | 606/9 |
| 2011/0046637 A1 * | 2/2011 | Patel et al. | 606/130 |

FOREIGN PATENT DOCUMENTS

| | | |
|---|---|---|
| EP | 1 302 172 | 4/2003 |
| WO | 2008/104914 | 9/2008 |

* cited by examiner

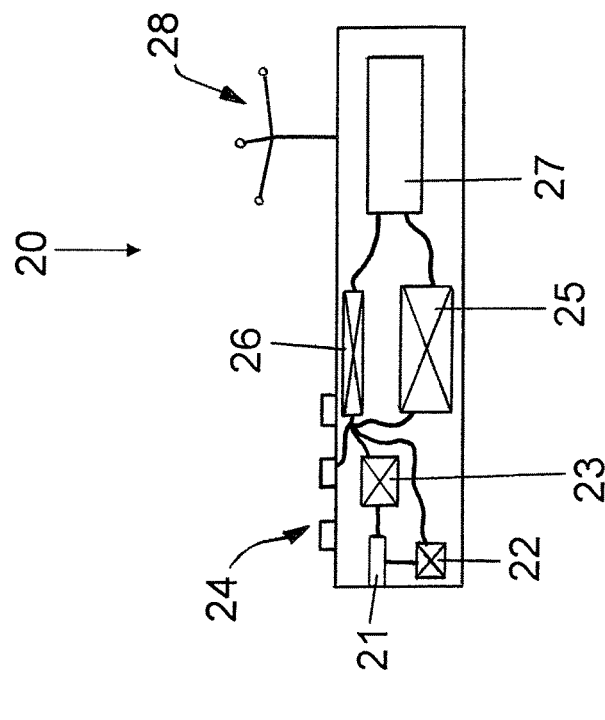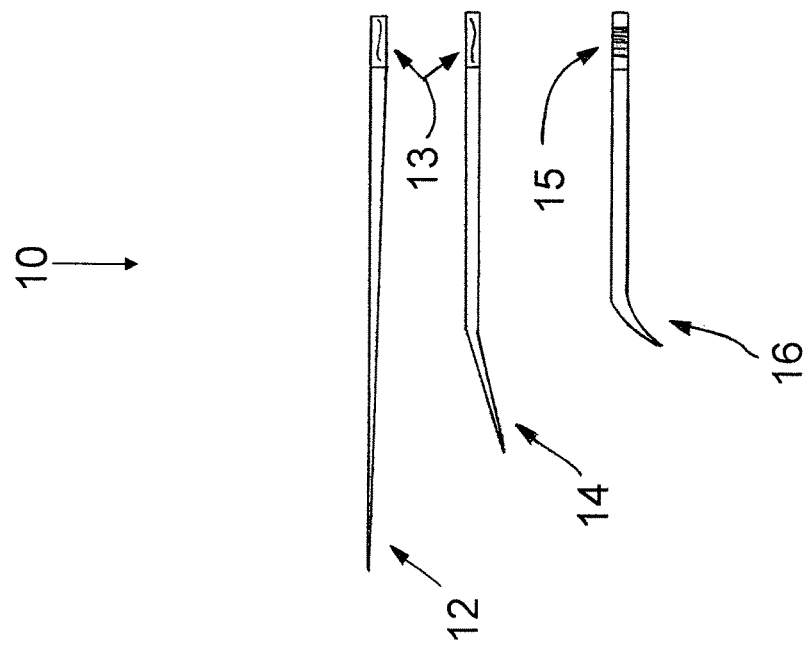
Figure 1

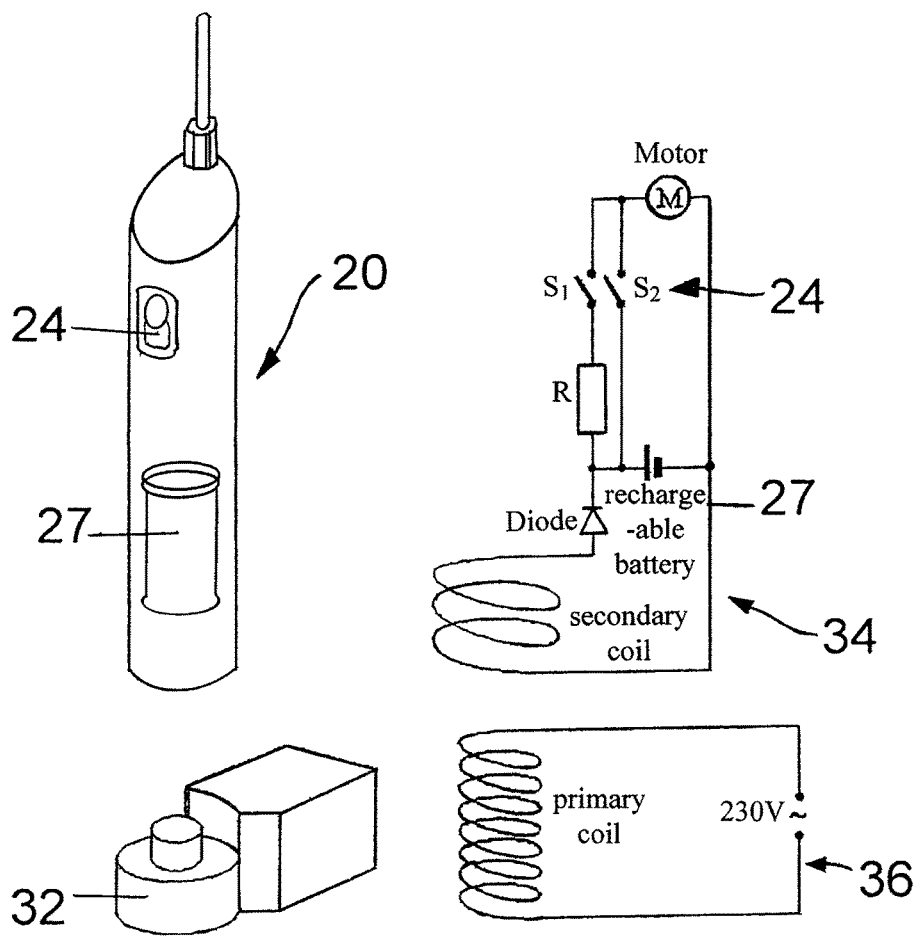
Figure 2A     Figure 2B
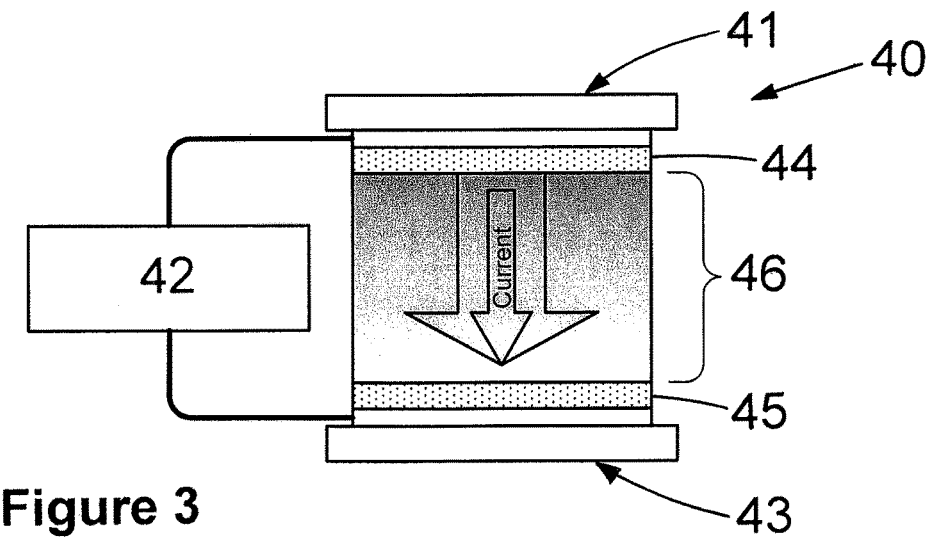
Figure 3

SURGICAL INSTRUMENT, IN PARTICULAR POINTER INSTRUMENT, COMPRISING TIP SENSOR

RELATED APPLICATION DATA

This application claims the priority of U.S. Provisional Application No. 61/104,799, filed on Oct. 13, 2008, which is hereby incorporated in its entirety by reference.

FIELD OF THE INVENTION

The invention relates to a surgical instrument, in particular a pointer instrument.

BACKGROUND OF THE INVENTION

Pointer instruments are widely used especially in the field of medical navigation, wherein this also applies to the instruments in accordance with the invention as described here. One specific type of use is to move the tip of the pointer instrument to points on the patient (landmarks) or on medical auxiliary devices, wherein calibrated or pre-calibrated pointer instruments are localized with the aid of a medical tracking system (for example via cameras and position markers on the instrument); the position of the tip of the instrument is thus known and therefore also the position of the landmark or, in very general terms, the point to which the pointer tip is moved.

Thus, this results on the one hand in a necessity to calibrate the instrument before it is used and/or a necessity to use a pre-calibrated instrument, the shape and dimensions of which—in particular, the position of the tip—has to be known to the navigation system. On the other hand, using such an instrument with a navigation system is in most cases still very operatively intensive, because the user always has to inform the navigation system that he is currently moving to a landmark, such that its position can be recorded and/or stored. If a number of points are successively recorded or a contour profile is continuously traveled using the pointer tip, difficulties can result because the navigation system constantly has to be informed as to whether the pointer tip is currently lying on the contour to be scanned or is being lifted and transferred to another location. If navigation is not "informed" in good time in the latter case, completely meaningless contour data is recorded during the transfer movement of the pointer.

SUMMARY OF THE INVENTION

It is the object of the present invention to provide a surgical instrument, in particular a pointer instrument, which makes handling with a medical navigation system simple and more user-friendly.

This object is solved in accordance with the invention by a surgical instrument comprising a handle portion and a tip, wherein a tip sensor is provided on the handle portion. The sub-claims define preferred embodiments of the invention.

In accordance with the present invention, a surgical instrument is thus provided, in particular a pointer instrument, which comprises a handle portion and a tip, and a tip sensor on the handle portion. The tip sensor is so-called because it detects various features which are associated with the tip of the instrument and which are explained in more detail below. In other words, the handle portion of the instrument in accordance with the invention is embodied such that it can detect information concerning the instrument tip, and precisely this characteristic of the instrument in accordance with the invention makes handling it very much simpler. For various information concerning the tip and/or its cooperation or interaction with the handle can be used in order to make navigation simpler, less elaborate and more user-friendly, because such information (for example concerning the type of tip or the current load on the tip) can replace information inputs which otherwise have to be made on the navigation system by the user.

Although a pointer instrument is a very good example of an instrument in accordance with the present invention, the invention is not limited to such pointer instruments. It can extend its advantages to any possible instruments, and examples of this include a broach comprising a handle and different tips, i.e. broach tips having for example different diameters or lengths. Another example of such a surgical instrument would be a bone saw which can use different exchangeable saw blades with a single handle.

In accordance with one embodiment of the present invention, at least one tip can be removably fastened to the handle portion, in particular using a releasable fastening, specifically a plug fastening. A number of tips can be exchangeably fastened to the handle portion, specifically by means of a fastening adaptor which is the same for a number of tips or for all the tips and allows the tips to be simply fastened and therefore also simply exchanged. Once fastened, the tip should sit on the handle rigidly and with zero tolerance.

The tip can comprise a handle fastening portion (which can also be the fastening adaptor) which complementarily cooperates with the tip sensor, and in accordance with one embodiment variant of the present invention, the tip sensor comprises a presence sensor for the presence of a tip. The presence sensor will in particular operate automatically, i.e. will determine the presence of a tip without being additionally operated, i.e. without user intervention.

It is however possible within the framework of the present invention not only for the presence of a tip to be determined but also for the tip and handle or one of the two elements to comprise a tip identifying device, in particular comprising a recognition device and/or reading-off device for the type and/or characteristics of the tip, wherein the device is assigned to the tip sensor, and comprising a recognition feature on the tip.

The tip identifying device can comprise a shape identification and/or shape key (for example in the manner of a door key), an RFID identification and/or a barcode identification. It is possible to embody the instrument such that the tip portion which interacts with the tip sensor, specifically the handle fastening portion comprising the recognition feature, bears information concerning the type and/or characteristics of the tip.

In accordance with another aspect of the present invention, the tip sensor comprises a force sensor for the force exerted by a tip on the handle portion. Using this force sensor, it is possible to detect whether the tip is currently pressing against a resistance and therefore whether the instrument is currently ready for use or is being used. It is thus possible for example to determine whether the tip is currently being moved to a landmark in order to detect its position. Detecting the force also allows detection over a longer period of time, such that it is possible to determine whether for example a pointer tip is sliding over a surface in order to detect its contour. The contour would then only be detected as long as a force by the tip on the handle is measured. When the instrument is removed from the surface, a force is also no longer exerted, and this can immediately and automatically switch off the contour detection in the navigation system.

Put in general terms, a functional interaction device is provided in a modification of the surgical instrument in accordance with the present invention and transmits data concerning the cooperation of the tip and the handle portion to a medical navigation system in order to assist in image-guided surgery, wherein the functional interaction device can comprise a data communicator, in particular a radio transmitter such as a Bluetooth or high-frequency and/or radio-frequency communicator/transmitter or an infrared, sonic and/or ultrasonic communicator/transmitter. A receiver for said communicated data can of course also be provided in a system attached in accordance with the invention, specifically a receiver for the data of the data communicator, which is connected to the medical navigation system.

The instrument can comprise an electrical energy supply, specifically comprising an energy store (battery, rechargeable battery) and/or an energy generator. In one embodiment, the rechargeable battery can specifically be charged in a non-contact process and/or by inductive charging. The energy generator can comprise one or more of the following devices: a piezoelectric energy generator; a thermo-electric energy converter; a solar cell energy converter.

In the following—up until the description of the figures—other general information concerning possible embodiments of a surgical instrument in accordance with the invention, specifically a pointer instrument for image-guided surgery, is also given.

The handle can be fitted with navigation markers, wherein specifically two or more reflective spherical markers can be provided. The geometry of the spherical marker array is dependent on the maximum length of the instrument tip. As an alternative to spherical markers, flat—for example circular—reflective layers can also be used.

As already mentioned, the tip interface is preferably embodied such that it can hold exchangeable tips which should be easy to exchange and fastened rigidly and/or with zero tolerance. With respect to detecting the tip, connected tips can preferably be automatically detected. This can be achieved with the aid of a key mechanism, i.e. the fastening mechanism is embodied like a car or house key which comprises an identification consisting of geometric data and a fixation to a device. The key shape can for example be provided on the tip side, while the handle is formed like a lock. A reverse arrangement is of course possible in principle.

If an RFID technique is used for identification, an energy-free RFID chip can be provided on the tip, while the RFID reader is situated in the handle. Alternatively, the reader could also be situated in the navigation station. If a barcode is used as a means of identification, it can be molded to the tip interface (injection-molding) or formed by laser engraving. A simple but durable imprint is of course also conceivable. A simple optical reading device would then be situated in the handle, which operates sequentially (code is read as the tip slides in), completely (code is read as a whole) or using remote detection in which the code is read by the navigation and/or tracking system. To this end, a dedicated reading device can be attached to the navigation and/or tracking system, or the tracking camera is used to read the code.

The status of the instrument tip connected to the handle can be regularly transmitted via a communication device, for example once a second, and different status information could be: "no tip provided"; "tip removed"; "tip inserted"; "unknown tip"; "tip detected" or "tip detected and OK".

A certain number of tips can be identified, and it is advantageous for this purpose to store the geometric tip data. The tip data is expediently stored and/or provided either in and/or on the tip itself or in the navigation system. In the former case, the data can be provided, encoded, in an identification device. The key can thus comprise both the identification and the tip data as shape information, and this data can also be stored in barcodes or RFIDs. It is also possible to accommodate all or some of the data in the navigation system, wherein for example the handle determines which tip is attached and the more specific data concerning the tip is then provided in the navigation system.

Basic information which comprises a mechanical description of the shape (vector graphics, splines, etc.) can be selected as the data format, or a complete 3D shape description (XML, VFML, STML). As already mentioned, a change of tip can be automatically relayed (detecting the tip, communication device). It is possible to identify a bent tip simply by checking it using the navigation software or by holding or pivoting it on a surface if—which is possible in accordance with the invention—not all the geometric data is stored for example in the software.

If a force sensor is used, it will measure the force which is exerted on the tip by measuring the force which passes from the tip to the handle portion. It is possible to indicate the pressure and/or force constantly on a navigation screen or also as an LED display (for example as fluorescent strips on the handle), advantageously comprising a green-yellow-red display sequence which shows non-critical, critical and excessive loads. This measurement of the force and/or pressure can also be used as a "switch", for example if surface-matching operations are performed and it is necessary to know at each moment whether the tip of the instrument is contacting something. When contacting the skin, the threshold for the force which indicates a contact would be low; in bone scans, this threshold would be higher. By measuring the force in this way, it is also possible to determine whether point acquisition is currently being performed on a bone or on a soft tissue (muscle, skin).

Metal or plastics may be considered as materials for the instrument tip; the tips can be disposable. The interface can be embodied as a standard interface for a number of handles or types of handles.

The communication between the instrument and the navigation system (IGS system=image-guided surgery system) can be unidirectional, i.e. when the handle is attached, sensor data is transmitted. The communication should have as few so-called line-of-sight problems as possible, which would be ensured in the case of radio communication. Sonic communication is however also conceivable, or infrared communication in which a tracking camera of the navigation system or a separate receiver is used as the receiver. Bidirectional communication is also possible, in which for example errors ascertained by the IGS system are indicated by LEDs on the handle.

Different buttons for controlling the navigation software can be attached to the handle, i.e. for example push-buttons, rocker switches or turning knobs (one to three, especially two to three buttons). They can be mechanical or electromechanical in nature or can be sensor buttons. They can have a tactile pattern on their surface so that they can be easily operated using surgical gloves.

Energy is needed for example for communication, for the sensor and the buttons, and batteries can be provided which are enclosed by the handle, can be sterilized along with it and exhibit a service life of several years. Exchangeable batteries are also conceivable, as are rechargeable batteries or thermo-electric elements which convert heat energy into electrical energy. The energy during the sterilization process could then in particular be used to charge the electrical energy supply. It is also possible to obtain energy by piezoelectric technology, wherein pressing a button could generate enough energy for example to support communication.

BRIEF DESCRIPTION OF THE DRAWINGS

The invention is explained in more detail below on the basis of different embodiments and with the aid of the enclosed drawings. It can comprise any of the features described here, individually and in any expedient combination. It can in particular also comprise specific uses of the devices shown or methods which are performed using them and presented here.

FIG. 1 shows a schematic representation of an instrument in accordance with the invention, comprising a number of exchangeable tips.

FIGS. 2A and 2B show a scheme for inductively charging energy.

FIG. 3 shows a scheme for thermo-electrically charging the instrument with energy.

DETAILED DESCRIPTION

FIG. 1 shows different alternatives of a surgical instrument, i.e. comprising different tips 12, 14, 16 (wherein the reference sign 10 is also used as a whole for the tip in general) and a handle portion 20. The tips can be different tips for a surgical pointer, wherein the tip 12 is a long straight tip, the tip 14 is a tip comprising an angled front part and the tip 16 is a rounded tip. All the tips have a fastening portion at the end opposite their front end, and in the case of the tips 12 and 14, this fastening portion 13 is formed as a key shape portion. The instrument tip 16 has a fastening portion 15 which has been provided with an engraved or imprinted barcode. The fastening portions 13, 15 serve on the one hand to fasten the tip to the handle, and on the other hand to identify the tip and to provide data, i.e. shape data, concerning the tip. Thus, the key portion 13 can comprise this data by mechanical shaping, while in the barcode of the portion 15, the data is accommodated in an encrypted form.

The tip 10 is connected by the fastening portion 13, 15 (adaptor) to the handle 20 which is shown here rather schematically and (to simplify presentation) somewhat distorted in its dimensions. The fastening portions of the tips 10 are inserted into the tip receptacle 21, where they are fastened. A first sensor 22 is assigned to the tip receptacle 21 and can on the one hand detect the presence of a tip and on the other hand—in specific embodiments—can also enable the tip to be identified via the information provided by the fastening portions 13, 15. If the receptacle 21 is complementarily formed as a lock for the key shape 13, a mechanical scan will both detect the presence of the tip and retrieve the additional information. In the case of the tip 16, the sensor 22 can comprise a barcode reader.

Another component in the handle 20 is the force sensor 23, using which the force and/or pressure which is exerted on the front end of the respective tip is determined via the force which is exerted by the tip on the sensor 23. As already described, this force information and/or pressure information can be evaluated in different ways, i.e. for example as a "switch" for point acquisition or area acquisition or as load information, wherein it is possible to differentiate whether the pointer is touching soft or hard tissue.

The reference sign 25 here represents another device which can be attached to the handle, for example an induction cell or solar cell for obtaining energy or a display (LED display) for the pressure values which are measured using the sensor 23. The reference sign 27 indicates an energy supply, i.e. a battery or a rechargeable battery, which is connected to the energy-generating or energy-consuming elements in the handle. A connection to the element 25, which as a solar cell or induction cell and/or piezoelectric cell can provide power to the energy supply 27, is for example representatively shown.

The handle comprises a data communicator or radio transmitter 26 so that information and/or data can be relayed from the handle. As indicated, all the elements and/or sensors 22, 23, 25 and the buttons 24 provided (for controlling the navigation software) are connected to said data communicator and/or radio transmitter 26 and provide it with data which it can relay to a navigation system, wherein the transmitter 26 of course consumes energy and is therefore likewise connected to the battery and/or rechargeable battery 27. Transmitted data can be identification data for the tips or pressure and/or force data of the sensor 23, or commands which are input via the buttons 24, or status data (level of charge in the rechargeable battery). The instrument can be a navigated instrument, as follows from the reference array 28 which is fastened to the handle and comprises three reflective spherical markers.

In a simple application scenario, the fastening portion 13 of the tip 12 is inserted into the receptacle 21 of the handle 20. The tip 12 is identified via the key information in the fastening portion 13 which is read off by the sensor 22. The data concerning the length of the tip and its shape is either provided directly by the information in the fastening portion 13 or is stored in the navigation system. Using this information concerning the tip 12, a "pre-calibrated" instrument consisting of the tip 12 and the handle 20 is so to speak provided, which can immediately be positionally detected by the navigation system and used for example for acquiring landmarks on a patient. During such acquisition, the pressure on the tip can for example be monitored using the sensor 23. If a landmark is acquired on the patient's skin, i.e. if it is to be positionally detected by the pointer tip, only a small pressure will be necessary using the pointer tip. If the pointer tip is pressed too firmly onto the landmark which is situated on the skin, the landmark (skin) could be shifted and the navigation result thus distorted. This pressure can however be monitored using the sensor 23, such that corresponding incorrect acquisitions can be avoided. The pointer is then for example only pressed onto the landmark in such a way that a fluorescent strip display 25 (here as an embodiment) indicates a green value.

Energy can be supplied and/or a rechargeable battery can be recharged as shown for example in FIGS. 2A and 2B. The instrument 20 has a rechargeable battery 27 which is welded in and tightly sealed such that the instrument can easily be sterilized. To this end, the handle 20 of the instrument is placed on the charging station 32, and the circuit diagrams on the right show how the charging station comprises a primary circuit 36 comprising a primary coil which inductively operates the secondary circuit 34 and charges the rechargeable battery 27 via the secondary coil. Such an embodiment comprising an enclosed rechargeable battery 27 is very advantageous with respect to sterilization.

A different form of energy supply is however also conceivable, i.e. obtaining energy thermo-electrically as shown for example and schematically in FIG. 3. The thermo-electric element 40 is provided in order to operate an electrical load 42 and comprises a heat source 41 and a cold sink 43. The heat source could for example be sterilization heat, while the cold sink is provided by the instrument which during sterilization is initially still cold. A so-called solid-state emitter 44 is connected to the heat source, and a thermo-electric semiconductor is situated between said solid-state emitter 44 and a solid-state collector 45 opposite. As long as there is a temperature gradient between the heat source 41 and the cold sink 43, the electrical load 42 can be operated—for example, the rechargeable battery 27 can be charged.

Such an energy generator could for example be integrated into the instrument handle, wherein the heat source would be outside and the cold sink would be inside or in the middle, where the instrument remains cool the longest.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A surgical instrument adapted to be repeatedly heat sterilized when exposed to an associated sterilizing heat source, the surgical instrument comprising:
    a handle portion;
    a tip;
    an energy generator and storage device configured to generate and store energy when the surgical instrument is heat sterilized, the energy generator and storage device comprising:
        a thermo-electric element comprising:
            a solid-state emitter:
            a solid-state collector; and
            a thermo-electric semiconductor disposed between the solid-state emitter and the solid-state collector, wherein the thermo-electric element selectively generates the energy responsive to a temperature gradient resulting from the surgical instrument being exposed to the associated sterilizing heat source, wherein the handle portion comprises a sink adjacent the solid-state collector; and
    a tip sensor provided on the handle portion, the tip sensor being operatively coupled with the energy generator and storage device and configured to distinguish between different tips based on a tip identifying device comprising at least one of a radio frequency identification (RFID), a shape identification, or a barcode identification, wherein the tip identifying device is configured to provide identification data from the tip to the tip sensor that allows the tip sensor to determine which one of the different tips is attached to the handle portion to facilitate use of the surgical instrument in an associated medical navigation system.

2. The surgical instrument according to claim 1, wherein the surgical instrument is a pointer instrument.

3. The surgical instrument according to claim 1, wherein at least one tip can be removably fastened to the handle portion.

4. The surgical instrument according to claim 3, wherein the at least one tip is fastened by means of a releasable fastening.

5. The surgical instrument according to claim 4, wherein the releasable fastening is a plug fastening.

6. The surgical instrument according to claim 1, wherein a number of tips can be exchangeably fastened to the handle portion.

7. The surgical instrument according to claim 6, wherein the tips are fastened by means of a fastening adaptor which is the same for a number of tips or for all the tips.

8. The surgical instrument according to claim 1, wherein the tip comprises a handle fastening portion which complementarily cooperates with the tip sensor.

9. The surgical instrument according to claim 1, wherein the tip sensor comprises a presence sensor for detecting the presence of a tip.

10. The surgical instrument according to claim 1, wherein a portion of the tip which interacts with the tip sensor includes information concerning at least one of a type or a characteristic of the tip.

11. The surgical instrument according to claim 10, wherein the tip comprises a handle fastening portion, the handle fastening portion comprises a recognition feature and includes information concerning at least one of a type or a characteristics of the tip.

12. The surgical instrument according to claim 1, wherein the tip sensor comprises a force sensor configured to measure a force exerted by the tip on the handle during use of the surgical instrument.

13. The surgical instrument according to claim 1, wherein a functional interaction device is provided which transmits data concerning the cooperation of the tip and the handle portion to the associated medical navigation system in order to assist in image-guided surgery.

14. The surgical instrument according to claim 13, wherein the functional interaction device comprises a data communicator.

15. The surgical instrument according to claim 14, wherein the data communicator comprises at least one of a radio transmitter, an infrared transmitter, a sonic transmitter or an ultrasonic transmitter.

16. The surgical instrument according to claim 1, wherein the energy generator and storage device further comprises a battery or a rechargeable battery.

17. The surgical instrument according to claim 16, wherein the battery or a rechargeable battery can be charged in at least one of a non-contact process or by inductive charging.

18. The surgical instrument according to claim 1, wherein the energy generator and storage device further comprises at least one of:
   a piezoelectric energy generator;
   or
   a solar cell energy converter.

19. A surgical system, comprising:
   the surgical instrument according to claim 12;
   a medical navigation system; and
   a data communicator operatively coupled with the force sensor and configured to communicate to the medical navigation system force data corresponding to a force measured during use of the surgical instrument,
   wherein the medical navigation system is configured to use the force data to identify contact with an object.

20. A system comprising:
   a surgical instrument adapted to be repeatedly heat sterilized by exposing the instrument to an associated sterilizing heat source, the surgical instrument comprising:
      a handle portion;
      a tip carrying identification data for identifying the tip;
      an energy generator and storage device configured to generate and store energy when the surgical instrument is heat sterilized, the energy generator and storage device comprising a thermo-electric element, the thermo-electric element comprising:
         a solid-state emitter;
         a solid-state collector; and
         a thermo-electric semiconductor disposed between the solid-state emitter and the solid-state collector, wherein the thermo-electric element selectively generates the energy responsive to a temperature gradient resulting from the surgical instrument being heat sterilized, wherein the handle portion comprises a sink adjacent the solid-state collector;
      a tip sensor provided on the handle portion, the tip sensor being operatively coupled with the energy generator and storage device and being configured to receive the identification data from the tip coupled with the handle portion based on a tip identifying device comprising at least one of a radio frequency identification (RFID), a shape identification, or a barcode identification; and
   a medical navigation system remote from the surgical instrument, wherein the medical navigation system is configured to:
      store tip data associated with a plurality of tips;
      receive the identification data corresponding to the tip coupled with the handle portion from the tip sensor; and
      process the received identification data to distinguish between different tips coupled with the handle portion and identify the tip data associated with the tip coupled with the handle portion to facilitate use of the surgical instrument in the medical navigation system.

21. A surgical instrument comprising:
   a handle;
   a plurality of tips, each of the plurality of tips being selectively coupleable with the handle;
   an energy generator including a thermo-electric element comprising:
      a solid-state emitter;
      a solid-state collector; and
      a thermo-electric semiconductor disposed between the solid-state emitter and the solid-state collector, wherein the thermo-electric element selectively generates energy responsive to a temperature gradient resulting from the surgical instrument being exposed to an associated source of sterilizing heat, wherein a portion of the handle comprises a sink adjacent the solid-state collector;
   an energy storage device operatively coupled with the thermo-electric element, the energy storage device being configured to store the energy selectively generated by the thermo-electric element; and
   a tip sensor provided on the handle, the tip sensor being operatively coupled with the energy storage device and configured to distinguish between the plurality of tips based on a tip identifying device comprising at least one of a radio frequency identification (RFID), a shape identification, or a barcode identification, wherein the tip identifying device is configured to provide identification data of each of the plurality of tips to the tip sensor that allows the tip sensor to determine which one of the plurality of tips is coupled with the handle to facilitate use of the surgical instrument in an associated medical navigation system.

* * * * *